US007622718B2

(12) United States Patent
Yoshimi et al.

(10) Patent No.: US 7,622,718 B2
(45) Date of Patent: Nov. 24, 2009

(54) RADIATION IMAGING CASSETTE

(75) Inventors: Takuya Yoshimi, Kanagawa-ken (JP); Eiichi Kito, Kanagawa-ken (JP); Tsuyoshi Tanabe, Kanagawa-ken (JP); Yasunori Ohta, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/232,884

(22) Filed: Sep. 25, 2008

(65) Prior Publication Data
US 2009/0078878 A1    Mar. 26, 2009

(30) Foreign Application Priority Data
Sep. 26, 2007    (JP) .............................. 2007-249027

(51) Int. Cl.
G21K 4/00    (2006.01)
(52) U.S. Cl. .................................. 250/370.08; 250/580
(58) Field of Classification Search ............ 250/370.08, 250/370.09, 580
See application file for complete search history.

(56) References Cited

U.S. PATENT DOCUMENTS

| 6,044,131 | A | * | 3/2000 | McEvoy et al. ............. 378/162 |
| 6,268,614 | B1 | | 7/2001 | Imai |
| 6,828,539 | B1 | | 12/2004 | Kuwabara |
| 2006/0017028 | A1 | * | 1/2006 | Ohara et al. ................. 250/580 |
| 2006/0280337 | A1 | | 12/2006 | Iwakiri et al. |
| 2007/0038402 | A1 | * | 2/2007 | Zhang ......................... 702/117 |

FOREIGN PATENT DOCUMENTS

JP    2005-176973    7/2005

* cited by examiner

*Primary Examiner*—David P Porta
*Assistant Examiner*—Marcus H Taningco
(74) *Attorney, Agent, or Firm*—Jean C. Edwards, Esq.; Akerman Senterfitt

(57) ABSTRACT

A radiation imaging cassette is provided with two types of communicating means within a housing. One is a wireless communicating means for communicating wirelessly with an imaging control means, and the other is a wired communicating means for communicating with the imaging control means. A metal detecting sensor for detecting metal in the periphery of the housing is also provided. A control section ceases the operation of the wireless communicating means and causes the radiation imaging cassette to communicate with imaging control means using the wired communication means, in response to detection of metal by the metal detecting sensor. Thereby, imaging operations are enabled to be performed safely even in cases that patients with pacemakers are in the vicinity of the radiation imaging cassette.

4 Claims, 4 Drawing Sheets

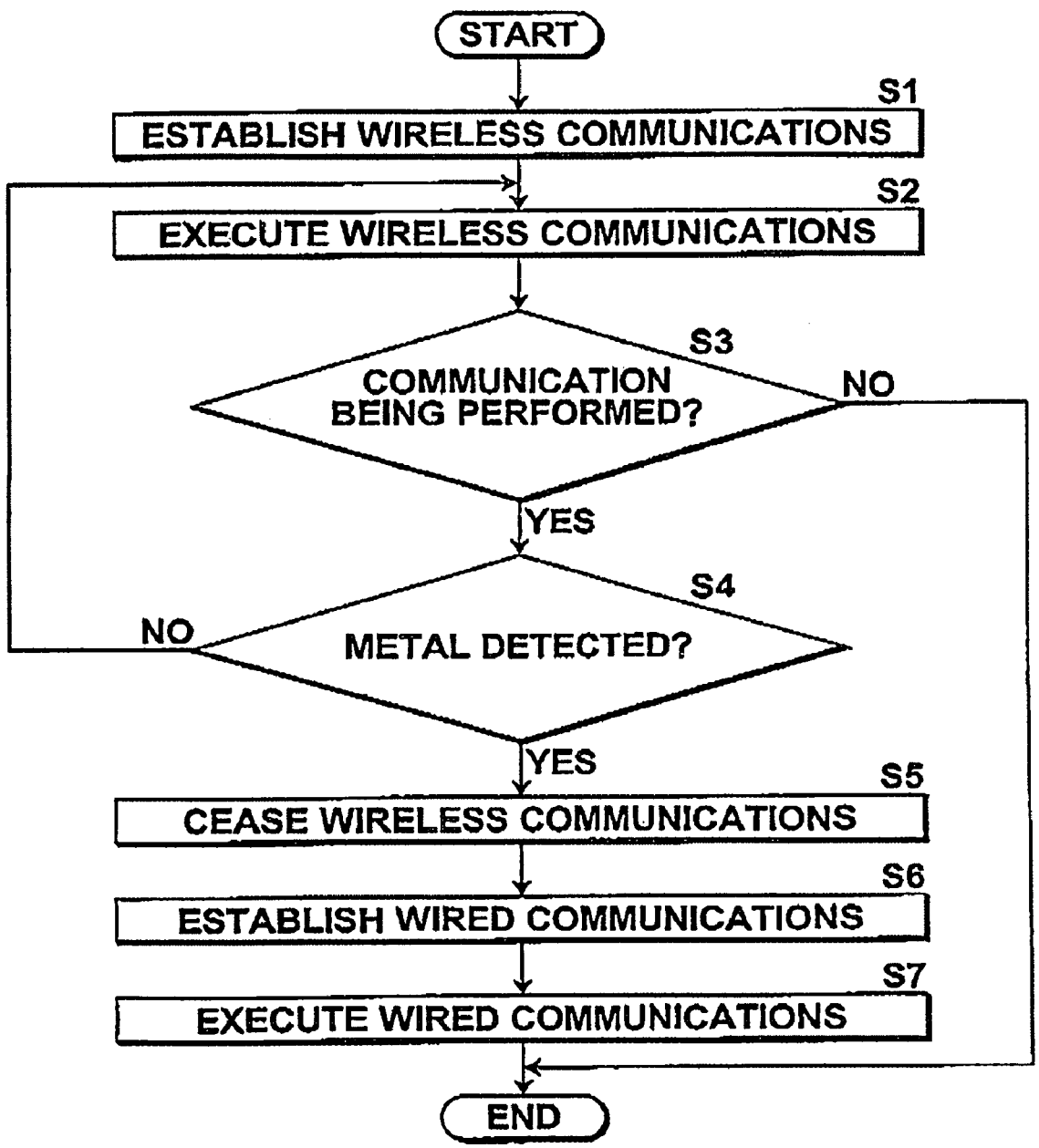

RADIATION IMAGING CASSETTE

CROSS-REFERENCE TO RELATED APPLICATIONS

The present application claims priority from Japanese Patent Application No. 2007-249027, filed Sep. 26, 2007, the contents of which are herein incorporated by reference in their entirety.

BACKGROUND OF THE INVENTION

1. Field of the Invention

The present invention is related to a radiation imaging cassette. More specifically, the present invention is related to a radiation imaging cassette which is capable of communicating with an external console that issues imaging commands.

2. Description of the Related Art

Presently, various radiation imaging apparatuses, for obtaining radiation images to be utilized for medical diagnoses and the like, have been proposed and are in practical use. These radiation imaging apparatuses employ solid state detectors (having semiconductors as main components thereof) as radiation image detecting means. The solid state detectors detect radiation that has passed through subjects, and obtain image signals that represent radiation images of the subject.

A variety of formats have been proposed for the solid state detectors to be utilized in these apparatuses. Regarding a charge generating process for converting radiation to electrical charges, there are solid state detectors of a photo conversion type, and solid state detectors of a direct conversion type, for example. A solid state detector of the photo conversion type temporarily stores signal charges, obtained at a photoconductive layer by detecting fluorescence emitted by phosphors due to irradiation with radiation, in a charge accumulating section, then converts the accumulated charges to image signals (electrical signals) and outputs the image signals. The direct conversion type of solid state detector temporarily stores signal charges, generated within a photoconductive layer due to irradiation with radiation and collected by a charge collecting electrode, in a charge accumulating section, then converts the accumulated charges to electric signals and outputs the electric signals. In this type of solid state detector, the main components are the photoconductive layer and the charge collecting electrode.

Regarding a charge readout process for reading out the accumulated charges, there are an optical readout method and a TFT readout method. In the optical readout method, accumulated charges are read out by irradiating a solid state detector with readout light (electromagnetic waves for readout). In the TFT readout method, accumulated charges are read out by scanning TFT's (thin film transistors), which are connected to a charge accumulating section. The TFT readout method is disclosed in U.S. Pat. No. 6,828,539.

An improved direct conversion type solid state detector has also been proposed in U.S. Pat. No. 6,268,614. The improved direct conversion type solid state detector is a solid state detector of the direct conversion type that utilizes the optical readout method. This solid state detector comprises: a recording photoconductive layer that exhibits photoconductivity when irradiated by recording light (radiation, or fluorescence generated by the irradiation of radiation); a charge transport layer that acts substantially as an insulator with respect to charges having the same polarity as latent image charges, and that acts substantially as a conductor with respect to charges having the opposite polarity as latent image charges; and a readout photoconductive layer that exhibits photoconductivity when irradiated by electromagnetic waves for readout; stacked in this order. Signal charges (latent image charges) that bear image information are accumulated at an interface (charge accumulating section) between the recording photoconductive layer and the charge transport layer. Electrodes (a first conductive layer and a second conductive layer) are provided on both sides of the three aforementioned layers. In the solid state detector having this format, the recording photoconductive layer, the charge transport layer, and the readout photoconductive layer are the main components.

Recently, various radiation imaging cassettes, in which the aforementioned solid state detectors are contained in small housings, have been proposed. These radiation imaging cassettes are comparatively thin and of portable sizes. Therefore, a radiation imaging cassette can be placed under a portion of a patient to be imaged, and a radiation source can be placed at a position that faces the radiation imaging cassette with the patient sandwiched therebetween, to perform imaging even if the patient is immobile. The radiation imaging cassettes enable imaging with a high degree of freedom.

There are radiation imaging cassettes which are connected to external consoles during imaging. Imaging information, such as patient ID information, is obtained by the radiation imaging cassettes from the external consoles, and obtained image data are transmitted from the radiation imaging cassettes to the external consoles after imaging operations. There are radiation imaging cassettes of this type that perform communications with the external consoles wirelessly, as disclosed in U.S. Patent Application Publication No. 20060280337.

In a radiation imaging cassette which is capable of communicating wirelessly with an external console, radio waves are constantly being transmitted while the cassette is powered ON, to establish communication with the external console. Therefore, there is concern that if the cassette approaches a patient who has a pacemaker implanted in his or her body, adverse influence may be exerted onto the pacemaker by the radio waves.

Japanese Unexamined Patent Publication No. 2005-176973 discloses a radiation imaging method that takes the influence exerted onto pacemakers by wireless communications into consideration. In this radiation imaging method, obtained images are analyzed, and wireless output is increased when it is confirmed that a pacemaker is not implanted in a patient. However, in this method, whether a pacemaker is implanted cannot be judged unless patients are imaged once. Therefore, the possibility of unexpected accidents occurring cannot be denied.

In view of the foregoing points, there is demand for a radiation imaging cassette which is capable of performing imaging operations safely, even in cases that patients with pacemakers are in the vicinity of the radiation imaging cassette.

SUMMARY OF THE INVENTION

The present invention has been developed in view of the foregoing circumstances. It is an object of the present invention to provide a radiation imaging cassette which is capable of communicating wirelessly with an external console that issues imaging commands, and capable of performing imaging operations safely, even in cases that patients with pacemakers are in the vicinity of the radiation imaging cassette.

A radiation imaging cassette of the present invention is capable of communicating wirelessly with an external console that issues imaging commands, and comprises: a housing that contains: a solid state detector that records image information when irradiated with radiation that bears the image information, a first communicating means for communicating wirelessly with the external console, a second communicating means for communicating with the external console in a manner other than wirelessly, and a control means for controlling the operations of the first communicating means and the second communicating means; and a metal detecting means for detecting metal in the periphery of the housing. The control means ceases the operation of the first communicating means and causes the radiation imaging cassette to communicate with the external console using the second communication means, in response to detection of metal by the metal detecting means.

Here, the phrase "communicating . . . in a manner other than wirelessly" refers not only to wired communications, but also to methods of wireless communication that do not adversely influence pacemakers, such as optical communications.

In addition, the term "solid state detector" refers to a detector that detects radiation that bears image information of subjects, and outputs image signals that represent radiation images of the subjects. The solid state detector converts radiation incident thereon to electrical charges, either directly or after converting the radiation to light. Image signals representing the radiation images of the subjects are obtained by outputting these electrical charges.

There are a variety of formats for the solid state detector. Regarding a charge generating process for converting X-rays to electrical charges, there is a photo conversion type of solid state detector, and a direct conversion type of solid state detector, for example. The photo conversion type of solid state detector temporarily stores signal charges, obtained at a photoconductive layer by detecting fluorescence emitted by phosphors due to irradiation with X-rays, in a charge accumulating portion, then converts the accumulated charges to image signals (electrical signals) and outputs the image signals. The direct conversion type of solid state detector temporarily stores signal charges, generated within a photoconductive layer due to irradiation with radiation and collected by a charge collecting electrode, in a charge accumulating portion, then converts the accumulated charges to electric signals and outputs the electric signals. Regarding a charge readout process for reading out the accumulated charges, there are an optical readout method and a TFT readout method. In the optical readout method, accumulated charges are read out by irradiating a solid state detector with readout light (electromagnetic waves for readout). In the TFT readout method, accumulated charges are read out by scanning TFT's (thin film transistors), which are connected to a charge accumulating portion. Further, there are solid state detectors that combine the direct conversion type and the optical readout method, such as the improved direct conversion type solid state detector, as disclosed in U.S. Pat. No. 6,268,614.

In the radiation imaging cassette of the present invention, it is preferable for the control means to cease the operation of the first communicating means and to cause the radiation imaging cassette to communicate with the external console using the second communication means, in response to reception of predetermined patient ID information from the external console.

It is also preferable for the first communicating means to communicate with the external console using UWB signals. However, various other existing communication protocols, such as Bluetooth, HiSWANa (High Speed Wireless Access Network type a), HiperLAN, wireless 1394, wireless USE, and wireless LAN, may be applied.

The radiation imaging cassette of the present invention is capable of communicating wirelessly with the external console that issues imaging commands, and comprises: the housing that contains: the solid state detector that records image information when irradiated with radiation that bears the image information, the first communicating means for communicating wirelessly with the external console, the second communicating means for communicating with the external console in a manner other than wirelessly, and the control means for controlling the operations of the first communicating means and the second communicating means; and the metal detecting means for detecting metal in the periphery of the housing. The control means ceases the operation of the first communicating means and causes the radiation imaging cassette to communicate with the external console using the second communication means, in response to detection of metal by the metal detecting means. Therefore, the metal detecting means can detect pacemakers without performing a single imaging operation, and wireless communications can be ceased. Accordingly, imaging operations are enabled to be performed safely even in cases that patients with pacemakers are in the vicinity of the radiation imaging cassette. Further, an alternative safe method of communications is enabled even in cases that wireless communications are ceased. Therefore, the utility and convenience of the radiation imaging cassette are maintained.

A configuration may be adopted, in which the control means ceases the operation of the first communicating means and causes the radiation imaging cassette to communicate with the external console using the second communication means, in response to reception of predetermined patient ID information from the external console. Therefore, even if there is a problem with the detection of the metal detecting means, wireless communications can be ceased based on the patient ID information. Accordingly, imaging operations can be performed more safely.

A configuration may be adopted, in which the first communicating means communicates with the external console using UWB (Ultra Wide Band) signals. In this case, the amount of power consumption is decreased, anti phasing properties are improved, and communication speed is improved over other communication protocols, which is advantageous.

BRIEF DESCRIPTION OF THE DRAWINGS

FIG. 4 is a flow chart that illustrates the processes performed during communication operations of the radiation imaging cassette of the present invention

BEST MODE FOR CARRYING OUT THE INVENTION

Figure 1:
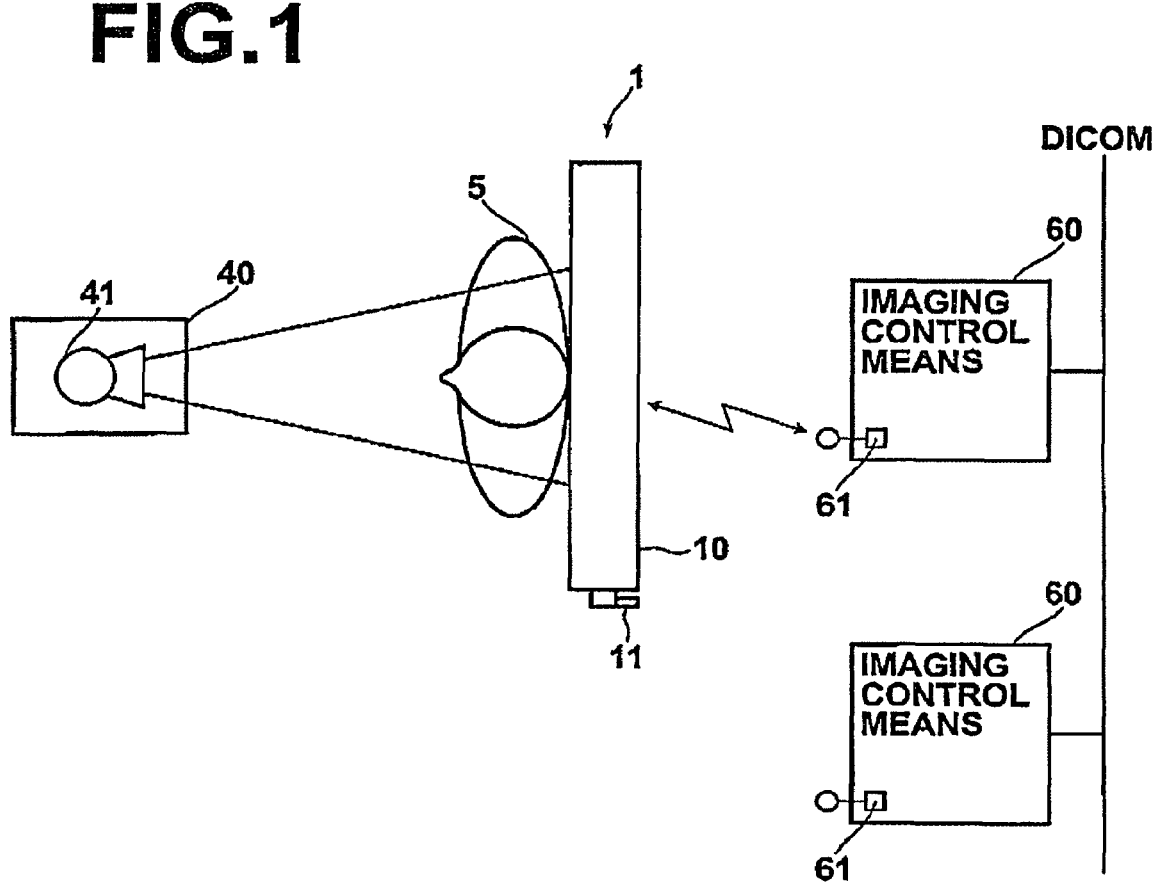
FIG. 1 is a schematic diagram that illustrates an example of a radiation imaging system that utilizes a radiation imaging cassette of the present invention.
Figure 2:
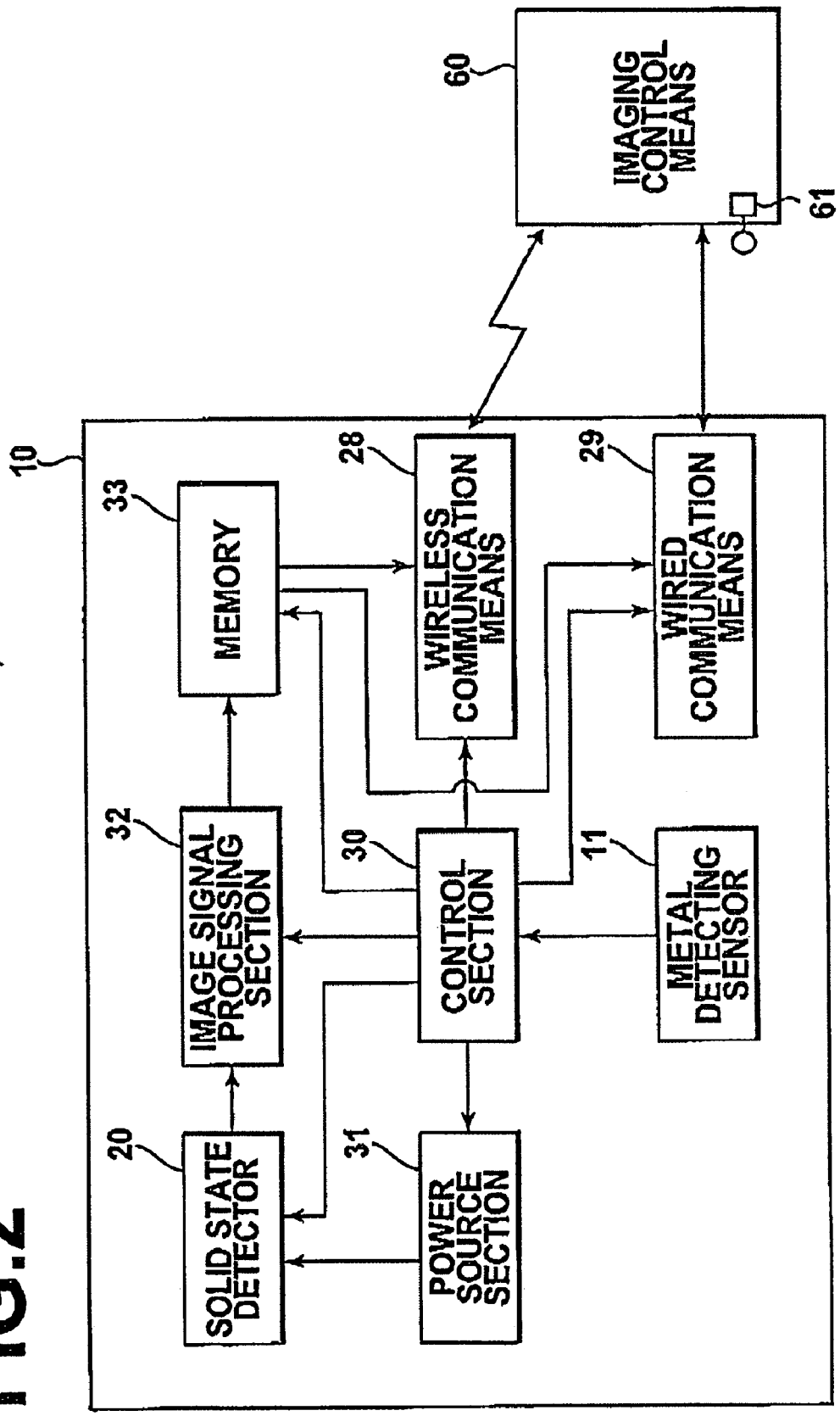
FIG. 2 is a schematic diagram that illustrates the radiation imaging cassette of the present invention.
Figure 3:
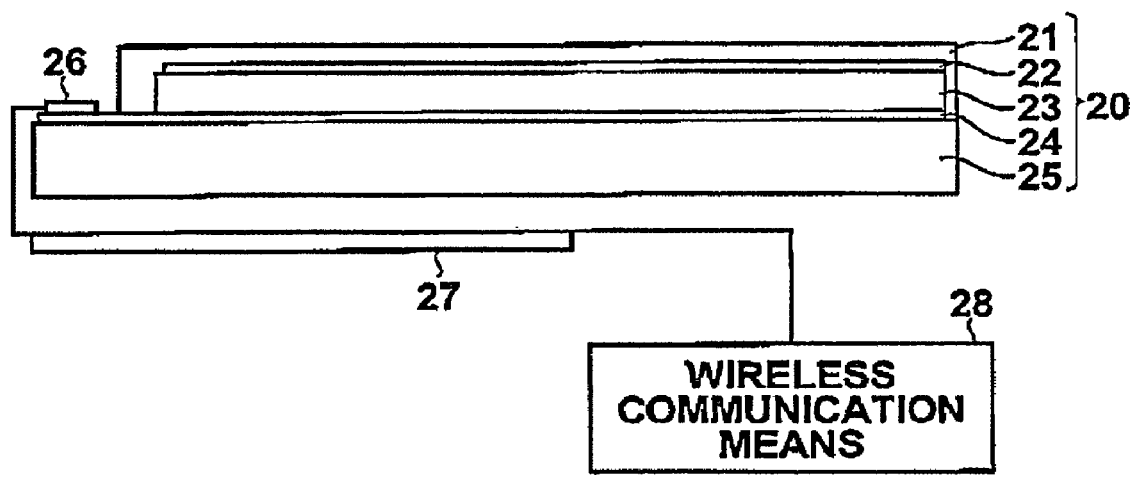
FIG. 3 is a schematic diagram that illustrates a solid state detector within the radiation imaging cassette of the present invention.

Hereinafter, an embodiment of the radiation imaging cassette of the present invention will be described in detail with reference to the attached drawings. FIG. 1 is a schematic diagram that illustrates an example of a radiation imaging system that utilizes the radiation imaging cassette of the present invention. FIG. 2 is a schematic diagram that illustrates the radiation imaging cassette of the present invention. FIG. 3 is a schematic diagram that illustrates a solid state detector within the radiation imaging cassette of the present invention.

The radiation imaging system is constituted by: a radiation imaging cassette 1, a radiation irradiating apparatus 40; and an imaging control means 60 (console). A solid state detector 20 and the like are provided within the radiation imaging cassette 1. A radiation source 41 for irradiating radiation toward the radiation imaging cassette 1 is provided in the radiation irradiating apparatus 40. The imaging control means 60 controls imaging operations and the like of the radiation imaging cassette 1.

The imaging control means 60 controls imaging operations and the like of the radiation imaging cassette 1, based on commands input by an operator. The imaging control means 60 is equipped with a communicating means 61 for communicating with the radiation imaging cassette 1. The imaging control means 60 is connected to a network, such as DICOM (Digital Imaging and Communication in Medicine).

The solid state sensor 20, which is an imaging device; an image signal processing section 32 that administers processes on signals output from the solid state detector 20; a memory 33 that stores image information; a wireless communicating means 28 for communicating wirelessly with the imaging control means 60; a wired communication means 29 for communicating with the imaging control means 60 via wires; a metal detecting sensor 11 for detecting metal in the periphery of a housing 10; a power source section 31 that supplies power to each of the above components; and a control section 30 for controlling the operations of each of the above components; are contained in the housing 10, as illustrated in FIG. 2.

The wireless communication means 28 communicates wirelessly with the imaging control means 60 using UWB (Ultra Wide Band) signals. The wired communication means 29 communicates with the imaging control means 60 via a LAN.

As illustrated in FIG. 3, the solid state detector 20 is formed by stacking: a first conductive layer 24 formed by a-Si TFT; a photoconductive layer 23 that generates electric charges and exhibits conductivity when irradiated with radiation; a second conductive layer 22; and an insulating layer 21 on a glass substrate 25, in this order.

A TFT corresponding to each pixel is formed on the first conductive layer 24. The output from each TFT is connected to an IC chip 26. The IC chip 26 is connected to the image signal processing section 32 on a printed circuit board 27.

The solid state detector 20 operates in the following manner. An electric field is formed between the first conductive layer 24 and the second conductive layer 22. If X-rays are irradiated onto the photoconductive layer 23 at this time, charge pairs are generated within the photoconductive layer 23. Latent image charges corresponding to the amount of charge pairs are accumulated within the first conductive layer 24. When reading out the accumulated latent image charges, the TFT's of the first conductive layer 24 are sequentially driven to read out analog signals corresponding to the latent image charges corresponding to each pixel. The analog signals for each pixel are detected by the image signal processing section 32, and composed in the arrangement order of the pixels. The composed analog signals are converted into digital image signals by an A/D converter (not shown). The generated digital image signals are output from the image signal processing section 32 to the wireless communication means 28 or the wired communication means 29 via the memory 33.

The wireless communication means 28 or the wired communication means 29 transmits the digital image signals to the imaging control means 60.

Next, the operation of the radiation imaging system will be described. Note that the operations of the radiation imaging cassette 1 are all controlled by the control section 30.

A communication ID signal is constantly being transmitted from the imaging control means 60, to establish communications with terminal devices, such as the radiation imaging cassette 1. When the communication ID signal is received, the radiation imaging cassette 1 outputs a response signal to the device (imaging control means 60) which is transmitting the communication ID signal, to establish communications therewith.

Communications between the radiation imaging cassette 1 and the imaging control means 60 are established in this manner. When an operator inputs commands indicating that an imaging operation is to be performed to the imaging control means 60, a REQUEST IMAGING signal is transmitted from the imaging control means 60 to the radiation imaging cassette 1.

When the REQUEST IMAGING signal is received, the radiation imaging cassette transmits an IMAGING READY signal to the imaging control means 60. When the IMAGING READY signal is received, the imaging control means 60 transmits an INITIATE IMAGING signal to the radiation imaging cassette 1.

When the INITIATE IMAGING signal is received, the radiation imaging cassette 1 causes voltage to be applied to the solid state detector 20.

When the operator depresses an IRRADIATE switch of the radiation irradiating apparatus 40 in this state, radiation is irradiated from the radiation source 41 toward the radiation imaging cassette 1.

When radiation is irradiated onto the radiation imaging cassette 1, latent image charges that bear the X-ray image information are accumulated within the solid state detector 20. The amount of accumulated latent image charges is substantially proportional to the X-ray dosage which has passed through a subject. Therefore, the latent image charges bear the electrostatic latent image.

The radiation imaging cassette 1 ceases application of the voltage onto the solid state detector 20 after a predetermined amount of time elapses, to complete imaging. Then, analog signals corresponding to the latent image charges are caused to be output from the solid state detector 20. The analog signals are A/D converted to generate digital image signals. The digital image signals which are generated by the image signal processing section 32 are output to the memory 33 in the order that they are generated.

When a portion of the digital image signals are transferred to the memory 33, a REQUEST IMAGE TRANSFER signal is transmitted to the imaging control means 60. When the REQUEST IMAGE TRANSFER signal is received, the imaging control means 60 transmits an IMAGE TRANSFER READY signal to the radiation imaging cassette 1.

When the IMAGE TRANSFER READY signal is received, the radiation imaging cassette 1 sequentially transmits the image signals stored in the memory 33 to the imaging control means 60. When all of the image signals stored in the memory 33 are transmitted to the imaging control means 60, the imaging operation is completed.

Normally, imaging is performed by the foregoing steps. However, in the case that the metal detecting sensor 11 detects metal in the periphery of the housing 10, a process for switching to wired communication is performed. This process will be described with reference to the flow chart of FIG. 4.

As described above, wireless communications are established (step S1), and wireless communications are performed between the radiation imaging cassette 1 and the imaging control means 60 (step S2). During the wireless communication, the radiation imaging cassette 1 monitors whether communications are being continued (step S3) and whether the metal detecting sensor 11 has detected metal (step S4) at a predetermined frequency.

In the case that it is judged that wireless communications have been completed at step S3, the process ends as described above.

In the case that the metal detecting sensor 11 detects metal in the periphery of the casing 10, it is judged that a patient with an implanted pacemaker is in the vicinity. In this case, the control section 30 ceases the operation of the wireless communication means 28 (step S5), and communications with the imaging control means 60 are performed by the wired communication means 29 (step S6).

At this time, an indicator (not shown) informs the operator that wireless communications have been ceased. In the case that the radiation imaging cassette 1 and the imaging control means 60 are not connected by a LAN cable, the operator is prompted to establish a connection with a LAN cable. After wired communications are established, the same processes as those which were performed using wireless communications are performed (step S7).

By adopting this configuration, imaging operations are enabled to be performed safely even in cases that patients with pacemakers are in the vicinity of the radiation imaging cassette.

Note that even in cases that the metal detecting sensor 11 does not detect metal in the periphery of the housing 10, if patient ID information indicating that a patient has an implanted pacemaker is received as imaging information, wireless communications are ceased, and communications between the radiation imaging cassette 1 and the imaging control means 60 are performed by wired communications.

A preferred embodiment of the present invention has been described above. However, the present invention is not limited to the above embodiment. For example the solid state detector may be that which employs the optical readout method. In addition, other protocols may be adopted for the wireless communication protocol and the wired communication protocol.

What is claimed is:

1. A radiation imaging cassette capable of communicating wirelessly with an external console that issues imaging commands, comprising:

a housing that contains: a solid state detector that records image information when irradiated with radiation that bears the image information, a first communicating means for communicating wirelessly with the external console, a second communicating means for communicating with the external console in a manner other than wirelessly, and a control means for controlling the operations of the first communicating means and the second communicating means; and a metal detecting means for detecting metal in the periphery of the housing;

the control means ceasing the operation of the first communicating means and causing the radiation imaging cassette to communicate with the external console using the second communication means, in response to detection of metal by the metal detecting means.

2. A radiation imaging cassette as defined in claim 1, wherein:

the control means ceases the operation of the first communicating means and causes the radiation imaging cassette to communicate with the external console using the second communication means, in response to reception of predetermined patient ID information from the external console.

3. A radiation imaging cassette as defined in claim 1, wherein:

the first communicating means communicates with the external console using UWB signals.

4. A radiation imaging cassette as defined in claim 2, wherein:

the first communicating means communicates with the external console using UWB signals.

* * * * *